United States Patent

Jones et al.

[11] Patent Number: 6,132,427
[45] Date of Patent: Oct. 17, 2000

[54] ELECTROSURGICAL INSTRUMENTS

[75] Inventors: Richard F. Jones, Winnetka; Scott B. Kerrigan, Hinsdale; Nels A. Sorensen, Zion, all of Ill.

[73] Assignee: MediCor Corporation, Vernon Hills, Ill.

[21] Appl. No.: 09/157,784

[22] Filed: Sep. 21, 1998

[51] Int. Cl.[7] .................................................. A61B 18/18
[52] U.S. Cl. .................................................. 606/45; 606/41
[58] Field of Search ........................... 606/32–34, 37–41, 606/45, 48; 600/372

[56] References Cited

U.S. PATENT DOCUMENTS

| | | | |
|---|---|---|---|
| 4,232,676 | 11/1980 | Herczog . | |
| 4,314,559 | 2/1982 | Allen . | |
| 4,492,231 | 1/1985 | Auth . | |
| 4,785,807 | 11/1988 | Blanch . | |
| 4,862,890 | 9/1989 | Stasz et al. . | |
| 4,876,110 | 10/1989 | Blanch . | |
| 5,380,320 | 1/1995 | Morris | 606/33 |
| 5,382,247 | 1/1995 | Cimino | 606/33 |
| 5,549,604 | 8/1996 | Sutcuet et al. | 606/45 |
| 5,693,050 | 12/1997 | Speiser | 606/41 |
| 5,702,387 | 12/1997 | Arts et al. . | |
| 5,713,895 | 2/1998 | Lontine et al. | 606/41 |
| 5,827,275 | 10/1998 | Morris | 606/41 |
| 5,885,281 | 3/1999 | Urueta | 606/45 |
| 5,925,039 | 7/1999 | Landingham | 606/41 |
| 5,925,043 | 7/1999 | Kumar et al. | 606/45 |
| 5,980,518 | 11/1999 | Carr et al. | 606/45 |

FOREIGN PATENT DOCUMENTS 2052657  2/1991  Canada .

*Primary Examiner*—Michael Peffley
*Attorney, Agent, or Firm*—Olson & Hierl, Ltd.

[57] ABSTRACT

An electrosurgical blade having an electrically insulating coating narrowly offset from the cutting edge and an optional porous polymeric coating on the cutting edge. The electrosurgical blade exhibits a bimodal temperature profile transversely across the blade, i.e., the blade is relatively hotter at the cutting edges as compared to the sides of the blade.

31 Claims, 2 Drawing Sheets

POSITION ON BLADE

ELECTROSURGICAL INSTRUMENTS

TECHNICAL FIELD OF THE INVENTION

This invention relates to electrosurgical instruments.

BACKGROUND OF THE INVENTION

Electrosurgery is the delivery of radio-frequency (RF) current through body tissue to raise tissue temperature for cutting, coagulating, and desiccating. With its first use dating back almost a century, electrosurgery has become common surgical practice.

In a typical application, electrical current is applied to preselected tissue using a unipolar electrode. The customary unipolar electrode consists of a stainless steel shaft or similar substrate that is substantially coated on its outer surface with an insulative (i.e., electrically nonconductive) coating. One end of the substrate is exposed for tissue contact.

During surgery, a return electrode is attached to the patient at a position away from the surgical area. A generator is then used to energize the electrode substrate. The exposed end of the electrode is brought into contact with preselected tissue of a patient which results in a current path being provided between the electrode and the patient. Current from the electrode develops a high temperature region about the electrode's exposed end which destroys tissue.

Coinciding with the rise in minimally invasive surgical procedures, recent development efforts in electrosurgery have principally centered on instruments suitable for closed procedures such as laparoscopy and endoscopy. Reflecting these efforts are the wide variety of specialized surgical electrodes now available. Examples include electrodes with a spatula tip, sling tip, scissor tip, forcep tip, cone tip, and button tip.

Somewhat left behind in these advancements has been the electrosurgical blade, or scalpel. Although they are used in the more traditional open surgical techniques, electrosurgical blades have in many respects more exacting performance requirements than electrodes used in closed procedures. The performance requirements for electrosurgical blades are more exacting because surgeons call upon these instruments to handle like a traditional scalpel.

A persistent problem with all surgical electrodes, especially noticeable and problematic for blade-style electrodes, is tissue sticking. Specifically, the electrosurgery causes charred tissue, commonly called "eschar," to adhere to the working surface of the electrode. For electrosurgical blades, the effect on handling from such stuck tissue mimics that of a dulled blade.

Numerous methods exist for providing a non-stick surface or coating to electrosurgical instruments. Unfortunately, the conventional non-stick coatings are also electrically insulative and therefore, not suitable for the working surface of electrosurgical blades.

Efforts at developing a conductive non-stick working surface for electrosurgical blades are the subject of other patents. For example, U.S. Pat. No. 4,785,807 to Blanch is directed to a stainless steel blade electrode completely covered by a coating of fluorinated hydrocarbon that is so thin it allows some conduction of radio-frequency electrical energy. This thin coating approach has at least two serious drawbacks. First, such thin coatings are not wear resistant and therefore, soon lose their non-stick effect. Second, it relies upon a capacitive coupling across the coating, a phenomena which both limits energy delivery and prevents uniform distribution of that energy.

There continues to be a need for improved electrosurgical blades that are durable yet surgeon friendly. In particular, there remains a need for an electrosurgical blade that overcomes the tissue sticking problem, without a corresponding drop in effectiveness for other performance criteria such as coagulation efficacy. To this end, it has now been found that the temperature profile transversely across the blade, i.e. between opposed cutting edges, is an important factor for optimizing blade performance.

SUMMARY OF THE INVENTION

A durable, user-friendly electrosurgical blade that resists degradation due to arcing comprises a conductive electrode substrate defining a longitudinal cutting edge, a radio frequency insulating coating on the blade but offset from the cutting edge, and an optional, porous polymeric coating on the insulating coating and/or the cutting edge. The optional polymeric coating provides a substantially hydrophobic conductive path to the cutting edge such that the electrical conductivity through the cutting edge is reduced by at least about 10 percent at 1 megahertz as compared to an uncoated edge but sufficient to provide at least coagulation current. The polymeric coating can be up to about 5 mils thick.

The electrosurgical blades of this invention exhibit a bimodal temperature profile transversely across the blade, i.e., the blade is relatively hotter at the cutting edges as compared to the sides of the blade. Thermographic scanning of an energized blade can be used during blade manufacture for quality assurance purposes.

DESCRIPTION OF THE PREFERRED EMBODIMENTS

Figure 1:
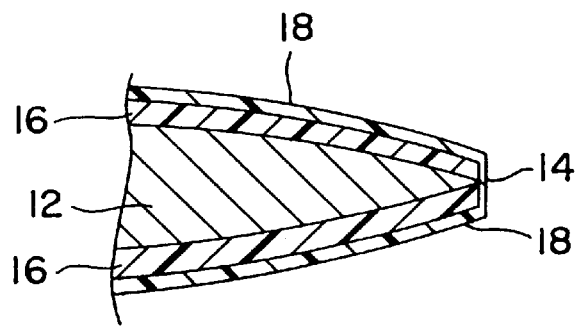
FIG. 1 is a sectional fragmentary view of an electrosurgical blade according to the present invention.

While this invention is susceptible of embodiment in many different forms, there are shown in the drawings and will be described herein in detail specific embodiments thereof with the understanding that the present disclosure is to be considered as an exemplification of the principles of the claimed invention and is not to be limited to the specific embodiments illustrated.

The present invention provides an electrosurgical blade with a substantially non-stick working surface. The electrosurgical blade has a radio frequency insulated portion as well as a conductive portion, and in use exhibits a bimodal temperature profile transversely across the blade.

As shown in FIG. 1, one preferred embodiment of an electrosurgical blade includes a conductive electrode substrate 12 that defines a longitudinal cutting edge 14, an insulating coating 16 and a porous polymeric coating 18. Polymeric coating 18 can be a fluorocarbon, a silicone, or a parylene coating, and can cover both cutting edge 14 as well as insulating coating 16, as desired.

Insulating coating 16 is offset from cutting edge 14. As used herein, the term "offset" means not completely covering. The exposed width of the cutting edge, i.e., not covered with insulating coating 16, is preferably in the range of about 0.05 millimeters to about 1 millimeter, but no more that about 2 millimeters.

Substrate 12 is conductive, and preferably a surgical grade stainless steel. Insulating coating 16 is substantially wear resistant, and provides insulation from energy in the radio frequency range (The range of 500 kilohertz to 1 megahertz is typical of electrosurgical generators.). Insulating coating 16 is preferably a ceramic such as a thermally applied alumina (aluminum oxide—$Al_2O_3$) or alumina composite such as alumina-chromia, although magnesium oxide, zirconia-yttria, zirconia-calcia, or the like can also be utilized. More specifically, a preferred ceramic coating has a dielectric strength of at least 1,000 volts/mm in the frequency range of 500 kilohertz to 1 megahertz, more preferably about 3,000 volts/mm. Suitable ceramic coatings are described in commonly owned U.S. Pat. No. 5,562,659 to Morris, the relevant portions of which are incorporated herein by reference.

So long as the necessary RF insulation effect is provided, the thickness of the insulating coating may vary to reflect a compromise among blade weight, cost, durability, and other competing factors. Where sprayed alumina is utilized, the preferred thickness is in the range from about 0.1 millimeters to about 0.3 millimeters.

An optional but preferred part of the present invention is a porous and substantially non-stick polymeric coating 18 on insulating coating 16 and cutting edge 14. Coating 18 provides a substantially hydrophobic conductive path to the cutting edge such that the electrical conductivity through the cutting edge at 1 megahertz is reduced by at least about 10 percent as compared to an uncoated cutting edge but sufficient to provide at least coagulation current.

Without violating this conductivity constraint, the thickness of the polymeric coating on the cutting edge may vary according to objectives for durability and non-stick characteristics. The preferred thickness of the polymeric coating for most applications has been found to be in the range of about 0.1 to about 0.5 millimeter.

In use, the porous polymeric coating at the cutting edge serves as a nucleation site for bubbling, i.e. water vapor in the form of bubbles at the blade-tissue interface.

A variety of polymeric materials are suitable for preparing electrosurgical blades according to this invention. A preferred polymeric coating is a fluorocarbon coating. One suitable type of fluorocarbon resin is polytetrafluoroethylene (PTFE) commercially available from the Whitford Corporation (West Chester, Pa.) under the designation "Xylan." A particularly preferred variety of PTFE is designated as "Xylan 8330H/831." Also suitable are the organic fluorocarbon materials sold by E. I. DuPont de Neumoirs under the designation "TEFLON."

The electrosurgical blade of this invention exhibits a bimodal temperature profile transversely across the blade, i.e., the blade is relatively hotter at the cutting edges as compared to the sides of the blade. Tissue proteins, including blood, can be coagulated with blade temperatures lower than those required for cutting and desiccating. In use therefore, the relatively cooler side portions of the electrosurgical blade of the present invention aid the surgeon by coagulating tissue without the sticking that is associated with tissue charring.

Although hotter in use than the side portions, the cutting edges of blades according to the present invention have a relatively small surface area. The relatively small area of interface between cutting edge and tissue also results in reduced sticking.

Figure 2:
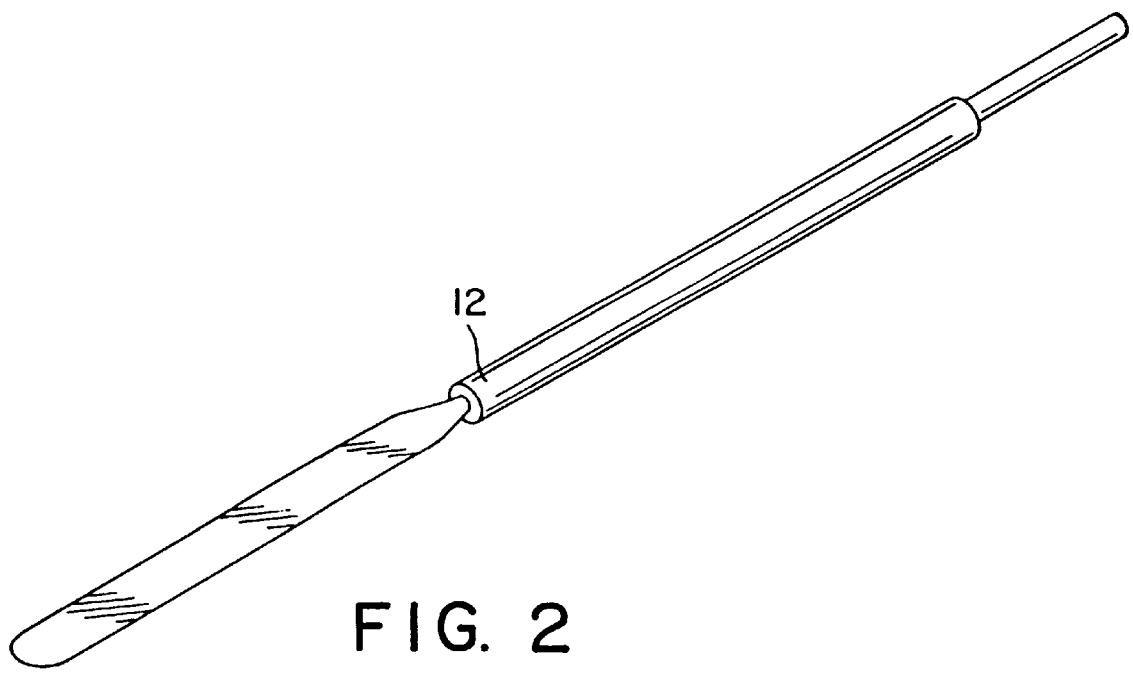
FIG. 2 is a perspective view of an electrode substrate suitable for fabricating electrosurgical blades according to the present invention.

One suitable approach for fabricating electrosurgical blades according to the present invention calls for a ceramic, insulating coating to be applied before a fluorocarbon coating. Specifically, a stainless steel, blade-shaped substrate as shown in FIG. 2 is first roughened by, for example, a grit blaster. The ceramic coating is then applied to the roughened substrate by thermal spraying, preferably using a plasma gun, a detonation gun, or a high-velocity oxygen fuel system. Optionally, a bonding underlayer (which may be molybdenum-powder) is applied to the substrate first before the ceramic coat to enhance bonding.

Next, the cutting edge of the blade is buffed to create an exposed surface in whole or in part. Optionally, the flat region of the blade may be buffed as well. The buffed blade is then dipped in uncured polytetrafluoroethylene (Xylan® 8330H/831) and then prebaked at 80° C. for about 5 minutes and cured in a kiln oven for about 25+30 minutes at 350° C. This dip and cure cycle may be repeated to increase the thickness of the fluorocarbon coating as desired. Variations in fabrication steps and coating compositions which do not adversely affect the insulative, conductive, and non-stick character of the electrosurgical blade will be evident to one skilled in the art, and are within the scope of this invention. For example, the blade may be sprayed with the fluorocarbon in lieu of dipping.

An optional, but preferred, step for the fabrication of electrosurgical blades according to this invention is a temperature profile inspection by thermographic analysis. Specifically, the electrosurgical blade candidate is evaluated thermographically while in actual or simulated operation to identify its temperature profile. Before inspection for temperature profile, fabricated electrosurgical blades are designated candidates. Candidates that do not exhibit the required bimodal temperature profile are rejected and discarded (or recycled).

The phrase "thermographic analysis," as used herein, refers to methods of sensing and displaying differences in the thermal radiation over selected dimensions of space. Examples of "thermographic analysis" include thermal imaging, infra-red imaging, infra-red scanning, etc. One suitable approach for implementing the temperature profile rejection test entails scanning the blade for radiation over the near infra-red spectrum while the blade is energized in a saline solution.

Figure 3:
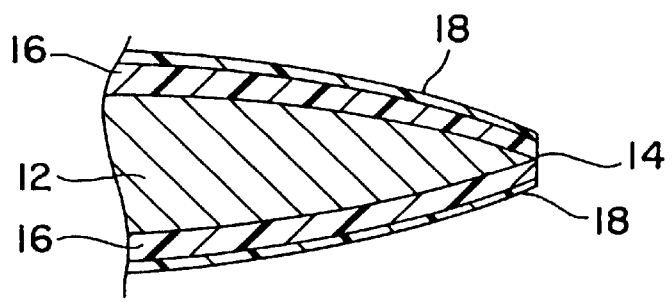
FIG. 3 is a sectional fragmentary view of an electrosurgical blade according to an alternate embodiment of the present invention.

FIG. 3 is a cross-section of an electrosurgical blade illustrating an alternate embodiment of the present invention. Here, the non-stick polymeric coating 18 is present on the insulating coating but removed from the cutting edge 14. The electrosurgical blade with a multi-layer coating and exposed cutting edge can be fabricated by further buffing of the cutting edge following the application of the polymeric coating.

Figure 4:
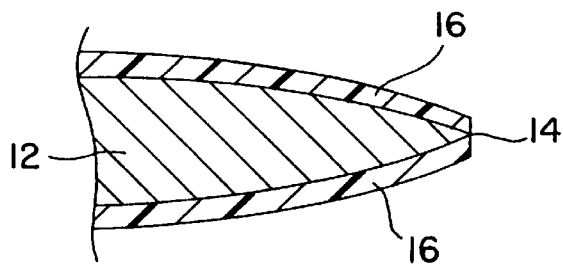
FIG. 4 is a sectional fragmentary view of an electrosurgical blade according to another alternate embodiment of the present invention.

FIG. 4 demonstrates an embodiment of the this invention without the optional, non-stick polymeric coating. Here, the insulating coating 16 is preferably smoothed by mechanical buffing.

Figure 5:
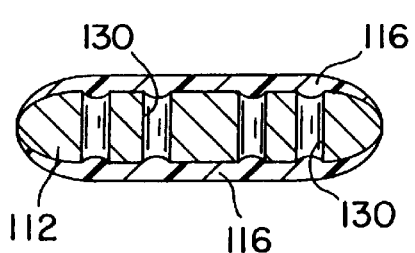
FIG. 5 is a sectional view of an electrosurgical blade according to yet another alternate embodiment of the present invention.
Figure 6:
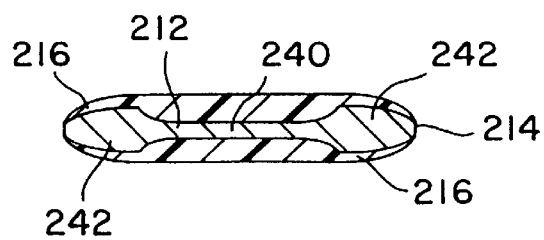
FIG. 6 is a sectional view of an electrosurgical blade according to yet another alternate embodiment of the present invention.

FIGS. 5 and 6 illustrate alternate embodiments of the present invention for accentuating the bimodal temperature profile. FIG. 5 is a cross-section of an electrosurgical blade having a perforated substrate 112 and radio frequency insulating coating 116. In use, the perforations 130 in substrate 112 limit the rate of heat transfer from the cutting edge to the sides, thereby increasing the related temperature difference.

FIG. 6 is a sectional view of an electrosurgical blade having a dog-bone shaped, or I-shaped, substrate 212 and insulating coating 216. Specifically, the substrate midsection 240 is relatively thinner than the edge-section 242, which is adjacent cutting edge 214. In use, the relatively thinner mid-section 240 serves to limit the rate of heat transfer from the cutting edge to the side section, thereby increasing the difference in operating temperature between the sides and the edges of the electrosurgical blade.

The present invention is further illustrated by the following examples.

EXAMPLE 1

Electrosurgical Blade for Use in Open Surgery

An electrosurgical blade according to the present invention was prepared as described above. More specifically, a ceramic coating of alumina was applied to a thickness of about 0.23 millimeters. The thickness of the fluorocarbon coating on the cutting edge was about 0.1 millimeter.

The effectiveness and user-friendliness of the electrosurgical blade was evaluated by testing with raw pork liver. The electrosurgical blade was tested for both cutting action and side (or flat) contact at both the 30-watt and 40-watt power levels and coagulating (COAG) or cutting (CUT) settings on a radio frequency (RF) generator. From these tests, assessments were made in the following performance categories: tissue adhesion, coagulation efficiency, thermal damage, and drag. Performance in each category was graded on a five point scale:

1—none or zero,
2—virtually none or very low,
3—slight or low,
4—moderate or average,
5—heavy or high.

Testing results are presented in TABLES 1 through 4, below.

EXAMPLE 2

Electrosurgical Blade with Buffed Ceramic Coating

An electrosurgical blade according to the present invention was prepared as described for EXAMPLE 1, except that the ceramic coating was also buffed before dipping in the fluorocarbon material. Effectiveness was evaluated as described in EXAMPLE 1. The results are presented in TABLES 1 through 4, below.

EXAMPLE 3

Electrosurgical Blade with Alternate Ceramic Thickness

An electrosurgical blade according to the present invention was prepared as described for EXAMPLE 1, except that a thinner ceramic coating was applied, about 0.15 millimeters. Effectiveness was also evaluated as described in EXAMPLE 1. The results are presented in TABLES 1 through 4, below.

EXAMPLE 4

Electrosurgical Blade

An electrosurgical blade was prepared that combines the variations present in EXAMPLES 2 and 3. For EXAMPLE 4, the ceramic coating was applied to a thickness of about 0.15 millimeter and then buffed before dipping in the fluorocarbon material. The electrosurgical blade was evaluated for effectiveness as described for EXAMPLE 1. The results are presented in TABLES 1 through 4, below

EXAMPLE 5

Comparative Performance

To further assess the relative effectiveness of electrosurgical blades according to the present invention, the performance of a buffed, but uncoated stainless steel blade electrode was also evaluated on pork liver as described in EXAMPLE 1.

TABLES 1 through 4 contain the results from the pork liver testing for the uncoated electrosurgical blade, together with such data for the blades of EXAMPLES 1 through 4.

TABLE 1

Side of Blade Laid Flat on Pork Liver At 30 Watts (COAG)

|  | Tissue Adhesion | Coagulation Efficacy | Thermal Damage |
| --- | --- | --- | --- |
| Uncoated Stainless Steel | 10 | 1 | 0 |
| Example 1 | n/a | 3 | 2 |
| Example 2 | 0 | 2 | 1 |
| Example 3 | n/a | 2 | 1 |
| Example 4 | 0 | 3 | 2 |

TABLE 2

Cut Across Pork Liver At 30 Watts (COAG)

|  | Drag | Tissue Adhesion | Coagulation Efficacy | Thermal Damage |
| --- | --- | --- | --- | --- |
| Uncoated Stainless Steel | 2 | 2 | 3 | 4 |
| Example 1 | 3 | 2 | 4 | 1 |
| Example 2 | 2 | 2 | 4 | 1 |
| Example 3 | 2 | n/a | 4 | 2 |
| Example 4 | 2 | 2 | 3 | 2 |

TABLE 3

Side Of Blade Laid Flat on Pork Liver At 40 Watts (CUT)

|  | Tissue Adhesion | Coagulation Efficacy | Thermal Damage |
| --- | --- | --- | --- |
| Uncoated Stainless Steel | 4 | 1 | 0 |
| Example 1 | 0 | 3 | 2 |
| Example 2 | 2 | 2 | 1 |
| Example 3 | 0 | 2 | 1 |
| Example 4 | 0 | 4 | 2 |

TABLE 4

Cut Across Pork Liver At 40 Watts (CUT)

| | Drag | Tissue Adhesion | Coagulation Efficacy | Thermal Damage |
|---|---|---|---|---|
| Uncoated Stainless Steel | 1 | 4 | 1 | 0 |
| Example 1 | 3 | 2 | 1 | 1 |
| Example 2 | 2 | 3 | 2 | 1 |
| Example 3 | 1 | 2 | 4 | 1 |
| Example 4 | 1 | 1 | 4 | 1 |

These data demonstrate that electrosurgical blades according to the present invention provide reduced tissue adhesion, while also providing equal or superior cutting and coagulation performance.

EXAMPLE 6

Thermographic Analysis

An electrosurgical blade according to the present invention was prepared as described above. Specifically, a stainless steel, blade-shaped substrate was first roughened by a grit blaster. The roughened substrate was primed with a bonding underlayer of molybdenum-powder. A ceramic coating was applied to the roughened and primed substrate by thermal spraying using a plasma gun (Plasmatron® Thermal Spray System Model #3700-$B_2$B-100-D). The average thickness of the ceramic coating on the blade substrate was about 0.23 millimeters.

The cutting edge of the ceramic coated blade substrate was then buffed to create an exposed surface. The flat ceramic coated region of the blade was also buffed for surface conditioning. The buffed blade was next dipped in uncured polytetrafluoroethylene (Xylan® 8330H/831), pre-baked for about 5 minutes at about 80° C. and then cured in a kiln oven for about 25-30 minutes at 350° C. After curing, the fluorocarbon coating was removed from the cutting edge by buffing.

The operational temperature profile of the electrosurgical blade was evaluated using an Agema Thermo-Vision 550 infra-red (IR) imager. To simulate operation, the blade was electrically energized at about 1 Mhz and 30 watts in a container of saline solution with a submerged return electrode. The blade tip was submerged about 0.5 cm and positioned such that one side of the blade formed about a 30 degree angle with the surface of the saline solution. The NIR imager was configured to scan the blade across its side, i.e. horizontally.

Figure 7:
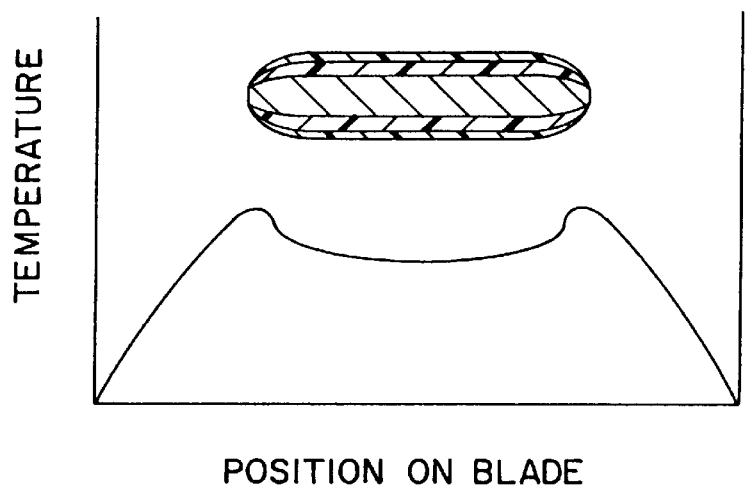
FIG. 7 is a combined graph and cross-section view showing the operational temperature profile of an electrosurgical blade according to the present invention.

Along with a qualitative visual analysis of the IR image, the temperature profile across the side of the blade was recorded and reproduced as FIG. 7. FIG. 7 demonstrates the advantageous bimodal temperature of electrosurgical blades according to the present invention. The bimodal profile is maintained during use in cutting and coagulating tissue. The relatively cooler side portions reduce sticking.

The foregoing specification is intended as illustrative and is not to be taken as limiting. Still other variations within the spirit and the scope of the invention are possible and will readily present themselves to those skilled in the art.

We claim:

1. A substantially planar electrosurgical blade exhibiting a substantially bimodal temperature profile comprising:

a perforated conductive electrode substrate defining a longitudinal cutting edge; and a radio frequency insulating coating on said blade but offset from said cutting edge.

2. The electrosurgical blade of claim 1 wherein said insulating coating is offset from said cutting edge no more than about 2 millimeters.

3. The electrosurgical blade of claim 1 wherein said insulating coating is offset from said cutting edge by a distance that varies over the length of said cutting edge from about 0.1 millimeter to about 3 millimeters.

4. The electrode of claim 1 wherein said insulating coating is a ceramic coating.

5. The electrosurgical blade of claim 4 wherein said ceramic coating is a thermally sprayed coating.

6. The electrosurgical blade of claim 1 wherein said insulating coating is a member of the group consisting of aluminum oxide, magnesium oxide, zirconia-yttria, zirconia-calcia, and alumina-chromia.

7. The electrosurgical blade of claim 1 wherein the thickness of said insulating coating is in the range of about 0.1 to about 0.3 millimeters.

8. The electrosurgical blade of claim 1 wherein said insulating coating has a substantially uniform thickness sufficient to provide an insulative capacity of at least about 1000 volts/millimeter over the 500 kilohertz to 1 megahertz frequency range.

9. The electrosurgical blade of claim 1 wherein said substrate is roughened stainless steel.

10. The electrosurgical blade of claim 1 wherein said substrate has an edge section adjacent said cutting edge and a mid-section, said mid-section being thinner than said edge section.

11. The electrosurgical blade of claim 1 wherein a porous polymeric coating is present on said cutting edge and said insulating coating, the polymeric coating providing a substantially hydrophobic conductive path to the cutting edge such that the electric conductivity through said cutting edge is reduced by at least about 10 percent at 0.5 megahertz as compared to an uncoated edge but sufficient to provide at least coagulation current.

12. The electrode of claim 11 wherein the radio frequency insulating coating is a ceramic coating.

13. The electrode of claim 11 wherein the radio frequency insulating coating is a alumina-chromia coating.

14. The electrode of claim 11 wherein the thickness of the porous polymeric coating is in the range of about 0.1 to about 0.5 millimeters.

15. The electrosurgical blade of claim 11 wherein said polymeric coating is a member of the group consisting of a fluorocarbon, a silicone, and a parylene.

16. The electrosurgical blade of claim 11 wherein said polymeric coating is a polytetrafluoroethylene coating.

17. A substantially planar electrosurgical blade exhibiting a substantially bimodal temperature profile comprising:

a conductive electrode substrate defining a longitudinal cutting edge; and a radio frequency insulating coating on said blade but offset from said cutting edge;

said substrate having an edge section adjacent said cutting edge and a mid-section, said mid-section being thinner than said edge section.

18. The electrosurgical blade of claim 17 wherein said insulating coating is offset from said cutting edge no more than about 2 millimeters.

19. The electrosurgical blade of claim 17 wherein said insulating coating is offset from said cutting edge by a distance that varies over the length of said cutting edge from about 0.1 millimeter to about 3 millimeters.

20. The electrode of claim 17 wherein said insulating coating is a ceramic coating.

21. The electrosurgical blade of claim 20 wherein said ceramic coating is thermally sprayed.

22. The electrosurgical blade of claim 17 wherein said insulating coating is a member of the group consisting of aluminum oxide, magnesium oxide, zirconia-yttria, zirconia-calcia, and alumina-chromia.

23. The electrosurgical blade of claim 17 wherein the thickness of said insulating coating is in the range of about 0.1 to about 0.3 millimeters.

24. The electrosurgical blade of claim 17 wherein said insulating coating has a substantially uniform thickness sufficient to provide an insulative capacity of at least about 1000 volts/millimeter over the 500 kilohertz to 1 megahertz frequency range.

25. The electrosurgical blade of claim 17 wherein said substrate is roughened stainless steel.

26. A substantially planar electrosurgical blade comprising:
- a conductive electrode substrate defining a longitudinal cutting edge;
- a radio frequency insulating coating on said blade but offset from said cutting edge; and
- a porous polymeric coating on said cutting edge and said insulating coating, the polymeric coating providing a substantially hydrophobic conductive path to the cutting edge such that the electric conductivity through said cutting edge is reduced by at least about 10 percent at 0.5 megahertz as compared to an uncoated edge but sufficient to provide at least coagulation current;
- said substrate having an edge section adjacent said cutting edge and a mid-section, said mid-section being thinner than said edge section.

27. The electrode of claim 26 wherein the radio frequency insulating coating is a ceramic coating.

28. The electrode of claim 26 wherein the radio frequency insulating coating is a alumina-chromia coating.

29. The electrode of claim 26 wherein the thickness of the porous polymeric coating is in the range of about 0.1 to about 0.5 millimeters.

30. The electrosurgical blade of claim 26 wherein said polymeric coating is a member of the group consisting of a fluorocarbon, a silicone, and a parylene.

31. The electrosurgical blade of claim 26 wherein said polymeric coating is a polytetrafluoroethylene coating.

* * * * *